United States Patent
Hickok

[11] Patent Number: 5,836,765
[45] Date of Patent: Nov. 17, 1998

[54] MICROENDODONTICS TITANIUM ULTRASONIC DENTAL TOOL

[76] Inventor: Teresa R. Hickok, 4106 Paseo De La Vista, Bonita, Calif. 91902

[21] Appl. No.: 825,328

[22] Filed: Mar. 28, 1997

Related U.S. Application Data

[63] Continuation-in-part of Ser. No. 766,787, Dec. 13, 1996.

[51] Int. Cl.[6] .............................. A61C 1/07; A61C 3/03
[52] U.S. Cl. ............................................ 433/119; 433/166
[58] Field of Search ................................ 433/86, 102, 81, 433/119, 165, 166

[56] References Cited

U.S. PATENT DOCUMENTS

| | | | |
|---|---|---|---|
| 2,831,132 | 4/1958 | Jackson | 310/26 |
| 2,990,616 | 7/1961 | Balamuth et al. | 433/119 |
| 4,223,676 | 9/1980 | Wuchinich et al. | 433/86 |
| 4,353,696 | 10/1982 | Bridges | 433/125 |
| 4,681,541 | 7/1987 | Snaper | 433/165 |
| 4,731,019 | 3/1988 | Martin | 433/119 |
| 4,832,683 | 5/1989 | Idemoto et al. | 433/119 |
| 5,094,617 | 3/1992 | Carr | 433/119 |
| 5,125,838 | 6/1992 | Seigneurin | 433/102 |
| 5,244,390 | 9/1993 | Lazzara et al. | 433/143 |
| 5,330,481 | 7/1994 | Hood et al. | 606/99 |
| 5,380,200 | 1/1995 | Heath et al. | 433/102 |
| 5,484,398 | 1/1996 | Stoddard | 433/119 |

FOREIGN PATENT DOCUMENTS

| | | | |
|---|---|---|---|
| 2566262 | 12/1995 | France | 433/119 |
| 1744148 A1 | 6/1990 | U.S.S.R. | |

*Primary Examiner*—Cary E. O'Connor
*Attorney, Agent, or Firm*—Baker & Maxham

[57] ABSTRACT

An ultrasonic dental tool for use with an ultrasonic transducer, comprises a substantially elongate tool defined by a shaft having a proximal end with a connector for attachment to an ultrasonic transducer, a distal end having a tip configured for performing a dental procedure, and a uniform gradual tapered portion intermediate the distal end and the proximal end is composed of a medical grade titanium alloy.

16 Claims, 4 Drawing Sheets

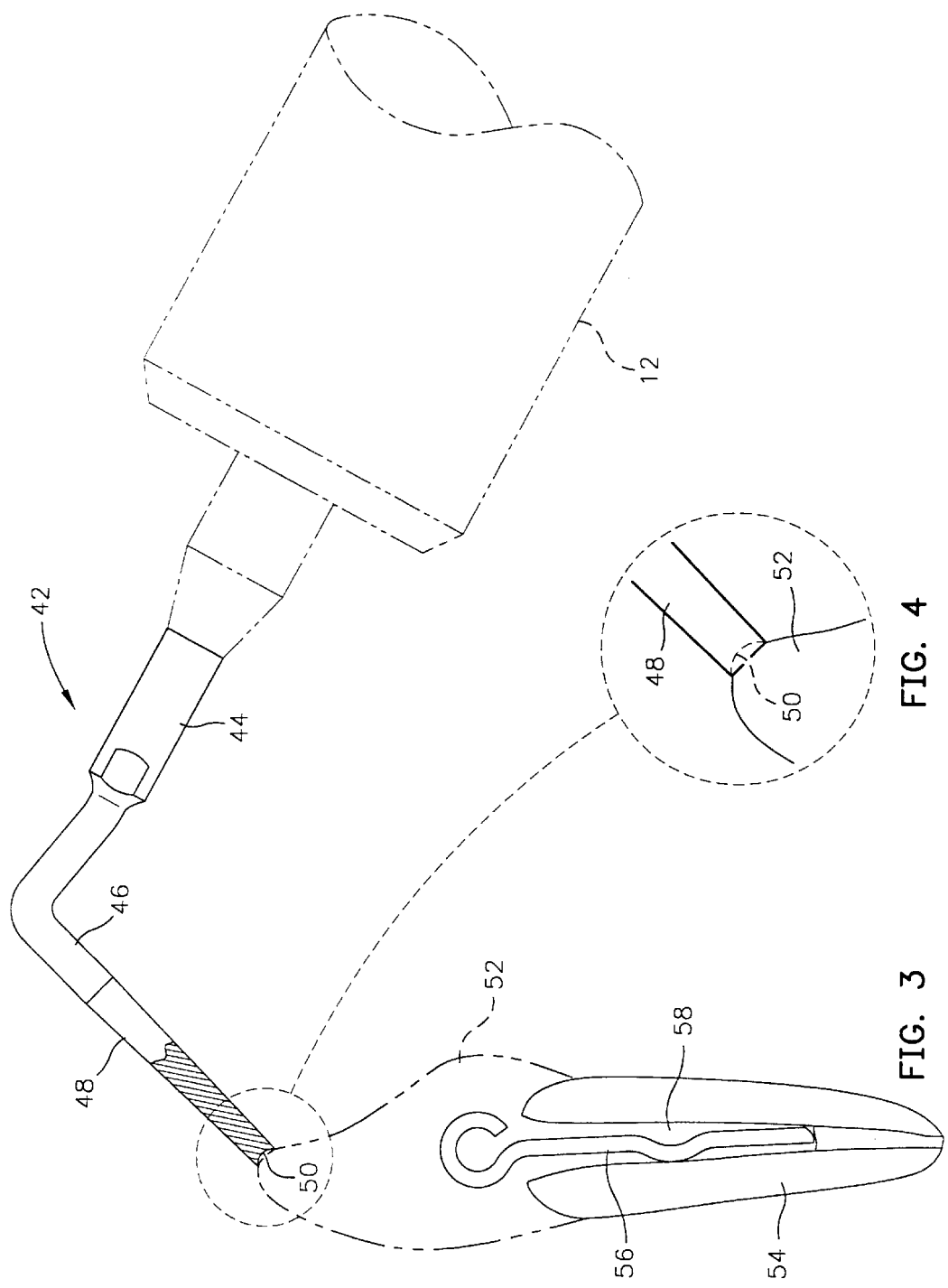

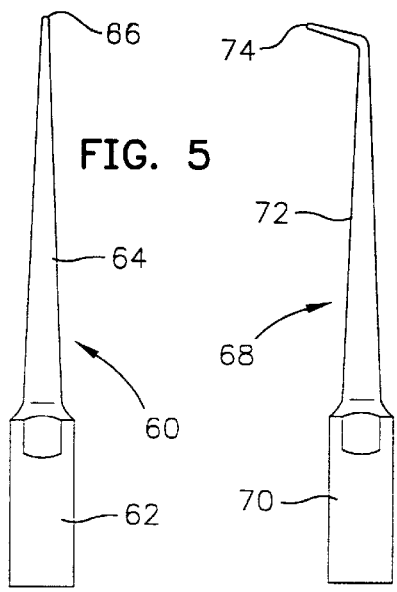

MICROENDODONTICS TITANIUM ULTRASONIC DENTAL TOOL

This application is a Continuation-in-Part of Ser. No. 08/766,787 filed Dec. 13, 1996, pending and entitled ULTRASONIC DENTAL TOOL.

FIELD OF THE INVENTION

This invention relates generally to ultrasonic dental tools and pertains more particularly to special ultrasonic surgical and dental tools.

BACKGROUND

Dental surgeons have in the past primarily used rotary drills with diamond cutting surfaces in the cutting, shaping and otherwise preparing teeth and bones. In recent years many dental surgeons have begun to use a tool usually called a tip coupled to an ultrasonic generator for many operations on teeth, bones, and soft tissue including dislodging and removal of dental material. These tools must be hard, durable and heat resistant in order to satisfactorily perform their function.

The tools normally used with ultrasonic generators are typically very small and must be hard and durable to withstand the high energy delivered by the ultrasonic generator. The tool must be constructed of a material that is capable of being shaped into the necessary or desired shape and then hardened. It must also be constructed of a medical grade of material to enable it to be used in the body. This typically means a good grade of stainless steel. These tools are usually constructed of a dental or medical grade of stainless steel which is hardened and then coated with diamonds or other hard material such as tungsten carbide.

Steel has been the predominant material for tools for centuries. This material in its many forms has many advantages and properties that make it ideal for working tools. It is relatively easy to fabricate into tools and can be hardened with alloys, coatings and heat treatment to make it hard and durable. Stainless steel in its many forms is the predominant material for medical and dental tools and instrument.

Titanium is a material that has been commercially available for less than twenty five years, but has become an important structural material because of an unusual combination of properties. The titanium alloys have strengths comparable to alloy steels while the weight is only about sixty percent of steel. Titanium is widely used in the aerospace industry where strength and weight are prime considerations. One significant use is for turbine rotor blades.

Recent years have seen greater use of ultrasonically powered instruments for the preparation of root canals. Examples of instruments of this type are disclosed in U.S. Pat. No. 4,019,254, issued Apr. 26, 1977 to Malmin, U.S. Pat. No. 5,094,617 issued Mar. 10, 1992 to Carr and PCT Publication WO 86/05967. With the exception of the first mentioned patent, all tools are formed with a shaft tapered to a point.

In the last three to four years microdentistry began to develop. Microdentistry is the performing of dental surgery and procedures with very small tools under a microscope. As an example, in the preparation of root canals, it has been found that the tool must be very small in order to work in the small canal areas. Such small tools must be very strong and tough and able to withstand and/or easily dissipate and/or resist heat.

Most dental tools and work areas are cooled with a continuous stream water during use. Cooling in this manner is not always possible, particularly when working in certain areas such as root canals, and in most instances this form of cooling is inconvenient.

Therefore, there is a need for an improved ultrasonic dental tool formed of a suitable strong, flexible and durable heat resistant material.

SUMMARY OF THE INVENTION

A primary objective of this invention is to provide an improved ultrasonic dental tool having a tip that is formed of durable high strength heat resistant material.

Another objective is to provide a tool of a suitable material that can be made small enough for microendodontics.

In accordance with a primary aspect of the present invention a dental tool for use with an ultrasonic transducer comprises a substantially elongate tool defined by a shaft having a proximal end with means for attachment to an ultrasonic transducer, and a distal end having a tip configured for performing a dental procedure, an intermediate portion, and formed of a medical grade of titanium.

BRIEF DESCRIPTION OF DRAWING

The objects, advantages and features of this invention will be more readily appreciated from the following detailed description, when read in conjunction with the accompanying drawing, in which:

FIG. 3 is an side elevation view of another embodiment of an ultrasonic dental tool shown in use;

FIG. 4 is an enlarged detailed view of the tool of FIG. 3;

FIG. 5 is an elevation view of a tool with a straight shank tapering to a point;

FIG. 6 is a view like FIG. 5 of a tool having a straight tapered shank extending down to an angled tip;

FIG. 7 is a view like FIG. 6 of a tool having a shank extending at an angle to the connector head tapering to a point;

FIG. 8 is a view like FIG. 7 where the shank tapers to a point with the shank having a contra-curve;

FIG. 9 is a view like FIG. 8 of a tool having an angled cylindrical body portion of a substantially uniform diameter extending to a necked down portion with a taper to a pointed tip angled to the opposite direction from the body;

FIG. 10 is a view like FIG. 9 with an angled cylindrical main body portion extending to a necked down tapered tip angled further in the same direction;

FIG. 11 is a view like FIG. 9 with a like body portion having a straight taper to a pointed tip;

FIG. 12 is a view like FIG. 11 having a tapered body portion offset to one side with a tip hooked in the opposite direction in substantially the same plane; and FIG. 13 is view like FIG. 12 of an embodiment like FIG. 12 with the hook in a plane other than that of the offset.

DETAILED DESCRIPTION OF PREFERRED EMBODIMENTS

Figure 1:
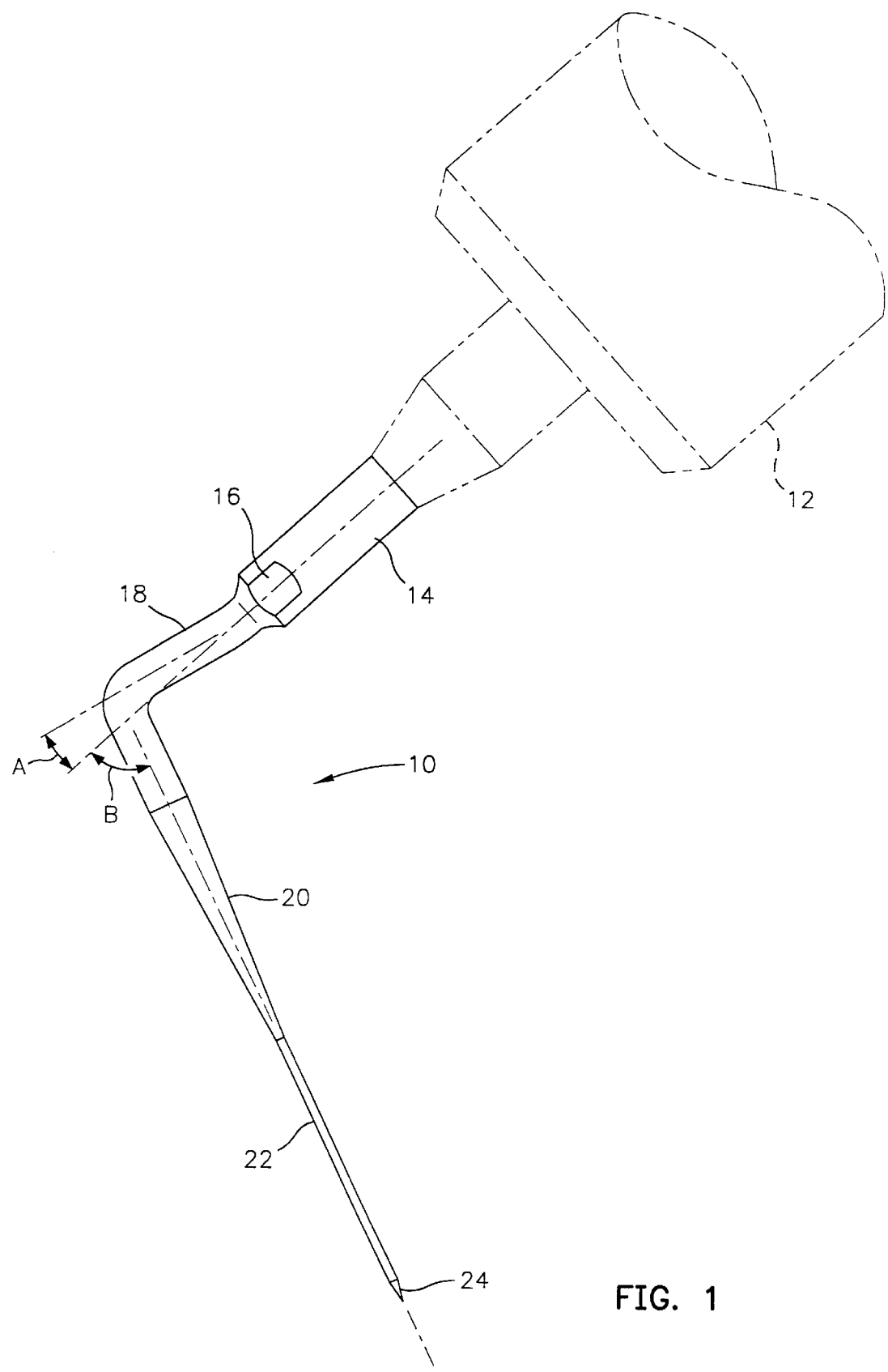
FIG. 1 is a side elevation view of an ultrasonic dental tool constructed in accordance with a preferred embodiment of the invention.

The present invention is described with reference to preferred embodiments of the invention as illustrated in the drawings. While this invention is described in terms of the best mode for achieving this invention's objectives, it will be appreciated by those skilled in the art that variations may be made in view of these teachings without deviating from the spirit or scope of the invention.

Referring to FIG. 1 of the drawings there is illustrated an exemplary embodiment of a tool for dental preparations, in accordance with the present invention, designated generally by the numeral 10. The tool 10 is designed for root canal work and is constructed of a medical grade titanium alloy. The inventor has found that titanium, which is not normally considered a tool material, performs well as a dental tip, particularly for ultrasonic generators. The tool is shown connected to an ultrasonic vibrator or transducer 12 (shown in phantom) of generally well-known conventional construction.

The tool, as illustrated, comprises an elongated shank having connecting means 14 at a proximal end. The connection means is shown in the form of a threaded socket for threadably mounting on the end of a shaft and having a flat 16 for engagement by a wrench or the like for threadably tightening and loosening the tool.

The tool has a proximal end portion 18 which is curved to form what is commonly called a contra-angle. This contra-angle portion is curved or bent in a first direction away from the axis of the proximal end at an angle A of about 15–25°, extending away from the proximal end. This contra-angle portion then curves or bends back across the axis of the proximal end or connection means at an angle B of about 70° to the axis of the connecting means.

The proximal portion 18 extends outward from the connecting collar 14 and is of a generally uniform diameter with the contra-angle curved in a manner, as illustrated. An intermediate portion or section 20 of the shaft tapers gradually down to a distal or working end portion 22, having a generally uniform cylindrical configuration extending from the intermediate portion 20 outward to a tip 24 which may have a sharpened point or other form. This portion 22 is the primary working portion and may have a length of from about 0.25 to about 0.394 inches or six to about ten or twelve (6–10/12) mm. When constructed of stainless steel this portion typically has a diameter of about 0.015 to about 0.0250 inches or about 0.4 to 0.6 mm when made of stainless steel. The length can be extended up to about 25 mm and the diameter about 0.015 inches or 0.4 to 0.6 mm when constructed of titanium.

The tool is constructed of a titanium alloy of a medical grade. Medical grade alloy means a material that may be used in contact with food and with a patients body without undergoing a chemical reaction. An alloy that the inventor has found preferable in the present application is identified as 6AL/4V ELI & CP Grade 4 and is available from President Titanium of Hanson, Mass. The inventor has found this material to be sufficiently hard, durable and flexible to resist breakage under use. It was also found to withstand heat for short durations of use in the absence of a cooling fluid without burning or melting. Tools can be made smaller with the titanium alloys than have ever been achieved before with the stainless steels. They can be made very small with very small tips that will withstand the rapid buildup of heat normally encountered in orthodontal applications.

Figures 2, 2A:
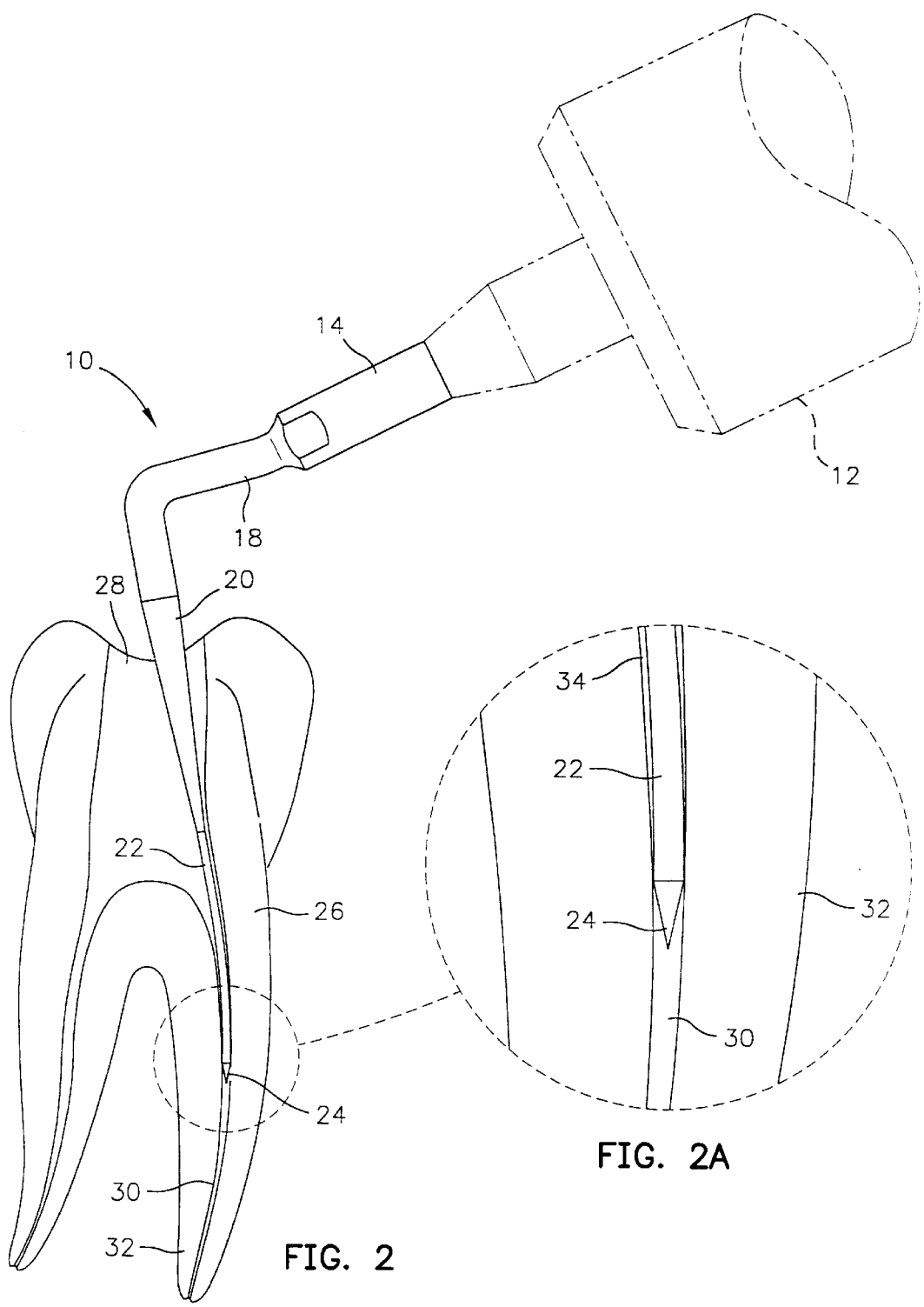
FIG. 2 is a view like FIG. 1 showing the tool in a root canal in a tooth.
FIG. 2a is an enlarged detailed view of the tip of the tool as shown in FIG. 2.

Referring to FIGS. 2 and 2A, the tool is designed to use in the preparation of tooth root canals. As illustrated, the tool is shown in use in a canal of a tooth 26 having an opening 28 in the crown of the tooth. The tool is inserted through the opening 28 and into a canal 30 of a root 32 of the tooth. As can be seen in FIG. 2A, the working distal end 22 of the tool is of a uniform cylindrical diameter throughout its length, such that when positioned in the tapered root canal 30, it provides space 34 around the shaft to enable the operator to view or see the wall area surrounding the tool as it's performing its work. This cylindrical shape doesn't wedge in the canal as does the tapered tool of the prior art. It also gives debris room (space 34) to move out of the canal. This construction made of titanium provides a tool having a working end 22 that is small, durable and flexible to enable insertion into a tooth 26 by way of a hole or bore 28 and work along root canal 30 of a root 32 as shown in FIGS. 2 and 2A.

The above-described alloy has about 5.5 to about 6.5% aluminum, about 3.5 to about 4.5% vanadium, about 0.25% of iron, about 0.05% nitrogen, about 0.08% of carbon and about 0.015% of hydrogen. This material has an ultimate tensile strength of about 130,000 psi, and a use strength of about 120,000 psi. It has a Rockwell-C hardness of 30/34. While this material has been known for uses such as for surgical appliances and implants, orthopedic implants and the like, applicant has found no suggestion of its use in dental tools, as set forth herein.

Other titanium alloys and their properties and specifications which may be suitable for the herein use are available from the aforementioned supplier. For example 6AL/4V, CP Grade 2 and CP Grade 4. Specifications for machining, heat treating and other technical data and specifications for manufacture and use of various alloys of titanium is available from President Titanium in a Machining and Technical data handbook. In many applications, applicant has found that these materials can be used for the tools herein without the necessity for heat treating.

The applicant has found that the titanium material discussed herein is suitable for a long-line of ultrasonic dental tools, as will be hereinafter described. Ultrasonic tools for dental work must be very small, durable and heat-resistant. Such tools must also be easily matched or tuned to an ultrasonic generator.

Referring to FIGS. 3 and 4, an alternate tool, designated generally by the numeral 42, is illustrated having the same overall contra-angle configuration as that of FIG. 1, but with a concave point or tip 50. The tool has a connector socket 44 with a contra-angle portion 46 and a tapered portion 48 and concave tip 50. This tool or instrument was conceived and designed to efficiently apply energy to the removal of crowns, bridges, posts and other materials. The tool with its concave tip 50 dramatically improves energy, clinical applications and efficiency when removing crowns, bridges, posts and other restorative materials. This concave shape in this instrument is unique as it allows more intimate contact and transference of ultrasonic energy to the obstruction, such as posts, crowns, epoxies and cements and restorative materials.

As illustrated in FIG. 3, the tool is applied to a crown 52 (shown in phantom) which is mounted on a portion of a tooth 54 by means of a post 56 cemented into a bore 58 of the tooth. As shown in detail in FIG. 4, the concave shape tip of this instrument provides a more intimate contact and transference of ultrasonic energy to the tooth crown or other obstruction.

Referring to FIG. 5, an ultrasonic tool having a straight tapered pointed configuration as illustrated, designated generally at 60 and comprising an elongated shank, having connecting means 62 at a proximal end with the shank tapering down at a reduced diameter from the connecting hub with a substantially uniform taper along a shaft 64 to a point 66. This tool may be used to perform any number of dental procedures and may be hardened or coated with suitable means for roughening or the like to create an abrasive surface, if desired.

Referring to FIG. 6, another embodiment is illustrated and designated generally by the numeral 68 having a connecting hub 70 with an elongated tapered shaft 72 down to a pointed tip 74 extending upward at an angle to close to 90° from the axis of the shaft 74. The angle of the tip may vary from less than 90° to greater than 90°, as desired. This tip may also be suitably roughened and coated as necessary to perform the necessary function.

Referring to FIG. 7, a tool 76 similarly has a connecting hub 78 with a tapered shaft 80 beginning with a bend immediately adjacent to the hub 78 and continuing down to a pointed tip 82. The curve of the shaft to the tip may be selectively positioned to increase the ability to gain access to selected work size.

Referring to FIG. 8, a tool 84 is illustrated having a connecting hub 86 with a continuous tapering shaft 88 down to a point 90. The shaft forms a gradual curve, first in a one direction with respect to the axis of the shaft, and then back with a gradual curve across the shaft to a straight section to the point 90. This shaped tool has been found to be useful scaling in tight interproximal areas.

Referring to FIG. 9, a tool 92 has the usual hub 94 with a first generally cylindrical shaft portion 96 with a neck down to a reduced diameter tapered shaft 98 to a sharpened point or tip 100. The tip in this instrument is illustrated extending substantially 90° to the axis of the shaft with the shaft bent over approximately 30° with respect to the axis of the coupling 94. This forms a hook and has been found useful in root canal work.

Referring now to FIG. 10, a similar constructed tool where the same elements are referred to by the same reference numerals is illustrated and wherein the tip is bent at an angle of approximately 90° in the opposite direction from that of the tool in FIG. 9. This forms a hook in the same direction as the angle of the main shaft of the tool.

Referring to FIG. 11, a somewhat similar tool 102 is illustrated having a similar shank or hub 104 with a generally cylindrical shank 106 extending at approximately 45° to the axis of the hub 104 and to a straight reduced diameter shaft portion 108 tapering uniformly down to a point 110.

Referring to FIG. 12, a tool is illustrated and designated generally by the numeral 112 and comprises a hub 114 with an offset shank formed of a generally straight first offset section 116 offset to one side of the axis of the mounting hub and tapering to a point 118 extending across in the opposite direction in substantially the same plane as the offset portion. This provides a useful root canal. The position and orientation of the tip enables it to provide access to remote teeth.

Referring to FIG. 13, a similar tool is illustrated and designated generally by the numeral 120 and comprising a hub 122 with an elongated shaft 124 which extends outward from the hub and is offset to one side as in the prior embodiment but with a tip 126 extending perpendicular to the offset shaft, but in a plane other than that of the offset. This provides yet another example of a tool to gain access to remote or distal teeth.

These tools may be modified in any number of ways to provide the best structure and features for performing various procedures, including scaling, drilling, root canal and the like. Various heat and other treating and hardening processes may also be utilized in preparing the various tools for their intended purposes. Likewise, various coatings may be applied to the tip to achieve its purpose.

A modification may be made wherein an ultrasonic dental tip is provided with a roughened area extending from near curved radius portion to pointed end. The roughened area provides a coarse abrasive surface that will cut along any part of the roughened surface.

Preferably the roughing of the surface is performed by sand blasting the desired area with a microetcher or microblaster using approximately 400 grit powder. A suitable choice for such a sandblaster is provided by Danville Engineering Inc., of Danville Calif., and is available by the model name of "S-2 Precision Microsandblaster." It is preferable to operate the sandblaster by supplying pneumatic pressure of about 60–120 pounds-per-square inch, although it will be apparent to one skilled in the art that a suitable hydraulic pressure could be provided.

The roughening of the tool surface is preferably carried out after any hardening and before any coating process. The roughening is a less expensive process than coating with diamond particles. It also enables the construction and preparation of more precise and accurate tips.

While the present instruments are primarily constructed to function without the need of water cooling and spraying, they may also be equipped with fine spray orifices or nozzles so that water or other cooling fluid may be introduced at the work site.

While we have illustrated and described our invention by means of specific embodiments, it is to be understood that numerous changes and modifications may be made therein without departing from the spirit and the scope of the invention as defined in the appended claims.

I claim:

1. A dental tool for use with an ultrasonic transducer, the tool comprising:

a substantially elongate tool defined by a shaft having a proximal end with attachment means at said proximal end for attachment to an ultrasonic transducer, and a distal end having a tip configured for performing a dental procedure; and said tool formed substantially uniformly throughout of titanium alloy of about 5.5 to about 6.5% aluminum, about 3.5 to about 4.5% vanadium.

2. The tool of claim 1, wherein said distal end is formed with a pointed tip.

3. The tool of claim 2, wherein said shaft has a continuous taper from said attachment means to said tip.

4. The tool of claim 3, wherein said shaft extends at an angle to the axis of said attachment means.

5. The tool of claim 4, wherein said shaft forms a contra angle.

6. The tool of claim 4, wherein said shaft forms a hook.

7. The tool of claim 2, wherein shaft has an intermediate cylindrical portion of about ten to about twenty millimeters in length.

8. The tool of claim 7, wherein said shaft is at an angle to said attachment means.

9. The tool of claim 8, wherein said shaft forms a contra angle.

10. The tool of claim 8, wherein said shaft forms a hook.

11. The tool of claim 1, wherein said distal end is formed with a concave tip.

12. A dental tool for use with an ultrasonic transducer, the tool comprising:

a substantially elongate tool defined by a shaft having a proximal end with attachment means at said proximal end for attachment to an ultrasonic transducer, and a distal end having a tip configured for performing a dental procedure; and said tool formed predominantly of a titanium alloy containing about six percent aluminum, and containing about four percent vanadium, wherein said shaft is roughened by minute depressions in the body of the shaft at least in an area adjacent the tip.

13. An ultrasonic dental tool for use in an ultrasonic transducer for dental procedures, the tool comprising:

an elongated tool defined by a shaft having a proximal end and a distal end, a connection member on said proximal end for attachment to an ultrasonic transducer, and a tip configured for performing a dental procedure on said distal end, and a substantially gradual tapered portion intermediate said connection member and said tip at said distal end, said shaft composed substantially uniformly throughout of a titanium alloy of about 5.5 to about 6.5% aluminum, about 3.5 to about 4.5% vanadium.

14. The tool of claim 13, wherein said shaft extends at an angle to the axis of said connection member.

15. The tool of claim 14 wherein said distal end is formed with a contra-angle portion curved outward in a first direction from said axis at an angle of about fifteen degrees and curved outward in a second direction across said axis at about forty-five degrees to said axis to said tip.

16. An ultrasonic dental tool for use in an ultrasonic transducer for dental procedures, the tool comprising:

an elongated tool defined by a shaft having a proximal end and a distal end, a connection member on said proximal end for attachment to an ultrasonic transducer, and a tip configured for performing a dental procedure on said distal end, and a substantially gradual tapered portion intermediate said connection member and said tip at said distal end, said shaft composed of a titanium alloy of about 5.5 to about 6.5% aluminum about 3.5 to about 4.5% vanadium, wherein said shaft has rough surface defined by minute depressions in the body of the shaft at least in an area adjacent the tip.

* * * * *